(12) United States Patent
Schnaibel et al.

(10) Patent No.: US 7,461,536 B2
(45) Date of Patent: Dec. 9, 2008

(54) CIRCUIT ARRANGEMENT FOR OPERATING A GAS SENSOR

(75) Inventors: Eberhard Schnaibel, Hemmingen (DE); Erich Junginger, Stuttgart (DE); Andreas Koring, Reutlingen (DE); Ruediger Deibert, Esslingen (DE); Harry Braun, Heimsheim (DE); Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 421 days.

(21) Appl. No.: 10/538,124

(22) PCT Filed: Sep. 24, 2003

(86) PCT No.: PCT/DE03/03168

§ 371 (c)(1),
(2), (4) Date: Jan. 6, 2006

(87) PCT Pub. No.: WO2004/053475

PCT Pub. Date: Jun. 24, 2004

(65) Prior Publication Data

US 2006/0137427 A1     Jun. 29, 2006

(30) Foreign Application Priority Data

Dec. 7, 2002   (DE) .................... 102 57 284

(51) Int. Cl.
*G01N 27/416*   (2006.01)
*G01N 27/419*   (2006.01)

(52) U.S. Cl. .................... 73/1.06; 204/401; 204/425

(58) Field of Classification Search .................. 73/1.03, 73/1.06, 23.31–23.32; 204/401, 406, 425, 204/427

See application file for complete search history.

(56) References Cited

U.S. PATENT DOCUMENTS

| | | | | |
|---|---|---|---|---|
| 4,532,013 A | * | 7/1985 | Dietz et al. | 204/401 X |
| 5,370,101 A | * | 12/1994 | Hamburg et al. | 123/688 |
| 5,423,203 A | * | 6/1995 | Namiki et al. | 73/1.06 |
| 5,488,858 A | * | 2/1996 | Achleitner | 73/1.06 X |
| 5,494,557 A | * | 2/1996 | Hotzel et al. | 204/425 X |
| 5,804,700 A | | 9/1998 | Kwon et al. | 73/23.32 |
| 6,059,947 A | | 5/2000 | Kato et al. | 204/425 |
| 6,073,083 A | * | 6/2000 | Schnaibel et al. | 702/65 |
| 6,099,717 A | * | 8/2000 | Yamada et al. | 204/401 X |

(Continued)

FOREIGN PATENT DOCUMENTS

DE   43 33 231   4/1995

(Continued)

OTHER PUBLICATIONS

*Spark-Ignition Engine Management*, Bosch Gasoline Engine Management, Vieweg Publishers, 1st ed. 1998, pp. 22-23.

*Primary Examiner*—Thomas P Noland
(74) *Attorney, Agent, or Firm*—Kenyon & Kenyon LLP

(57) ABSTRACT

A circuit configuration for operating a gas sensor is described, including a reference gas space in which an electrode is situated which is supplied with a reference gas pump current to maintain the concentration of the reference gas. A diagnostic system determines a concentration change of the reference gas via a change in the reference pump current and a time-based evaluation of the sensor signal of the gas sensor.

12 Claims, 2 Drawing Sheets

U.S. PATENT DOCUMENTS

| | | | |
|---|---|---|---|
| 6,120,663 A * | 9/2000 | Kato et al. | 204/401 |
| 6,294,075 B1 * | 9/2001 | Poggio et al. | 204/406 X |
| 6,439,038 B1 * | 8/2002 | Rosel et al. | 73/117.3 |
| 6,471,840 B1 | 10/2002 | Gao et al. | 204/425 |
| 6,482,310 B2 * | 11/2002 | Detwiler et al. | 205/784.5 |
| 6,711,932 B2 * | 3/2004 | Iwazaki et al. | 73/1.06 |
| 6,935,155 B2 * | 8/2005 | Yasui et al. | 73/1.06 |

FOREIGN PATENT DOCUMENTS

| | | | | |
|---|---|---|---|---|
| DE | 196 36 226 | | 3/1998 | |
| JP | 59160747 A | * | 9/1984 | 73/1.03 |
| JP | 59168357 A | * | 9/1984 | 73/1.03 |
| JP | 63304151 A | * | 12/1988 | 73/31.05 |
| JP | 07166940 A | * | 6/1995 | |
| JP | 08105343 A | * | 4/1996 | |
| JP | 09137717 A | * | 5/1997 | |
| JP | 2000097893 A | * | 4/2000 | |

* cited by examiner

CIRCUIT ARRANGEMENT FOR OPERATING A GAS SENSOR

FIELD OF THE INVENTION

The present invention is directed to a circuit configuration for operating a gas sensor.

BACKGROUND INFORMATION

A circuit configuration which supplies a signal obtained via a gas sensor that is a measure of the lambda air factor in the exhaust gas of combustion processes is described in the technological book "Ottomotor-Management/Bosch" [Bosch Gasoline Engine Management] Vieweg Publishers, $1^{st}$ edition 1998, pages 22-23. The gas sensor has a pump cell situated between a first electrode and a second electrode. The first electrode is exposed to the exhaust gas. The second electrode is situated in a measuring gas space which is acted upon by the exhaust gas via a diffusion barrier. The second electrode together with a third electrode situated in a reference gas space forms a Nernst cell which supplies an almost abrupt voltage change in the area of a stoichiometric gas mixture present at the second electrode of the Nernst cell. The reference gas space is filled with oxygen as the reference gas. The required oxygen concentration in the reference gas space is adjustable using a reference pump current, which is supplied to the third electrode in the reference gas space. The reference pump current results in an oxygen ion transport out of the measuring gas space of the Nernst cell into the reference gas space.

A difference amplifier compares the voltage occurring at the Nernst cell with a reference voltage, which is set at approximately 450 mV, corresponding approximately to the middle of the voltage jump of the Nernst cell. The difference amplifier sets a pump cell pump current which is supplied to the first electrode. The pump cell pump current results in an oxygen ion transport in the pump cell which attempts to keep the oxygen content in the measuring gas space at a level at which a stoichiometric mixture prevails. The pump cell pump current may be used as the output signal of the gas sensor. It corresponds to a measure of the lambda air factor in the exhaust gas.

The oxygen concentration in the reference gas space varies constantly due to diffusion processes. Oxygen ions are diffusing out of the reference gas space while hydrocarbons are diffusing into the reference gas space. The two processes result in an unwanted decline in the oxygen concentration, which is known as poisoning of the reference gas space.

German Published Patent Application No. 43 33 231 describes a method for operating an oxygen sensor having an internal pumped reference in which the reference pump current is increased temporarily under certain operating conditions to eliminate any poisoning that might already be present or to prevent imminent poisoning.

An unwanted change in the oxygen concentration in the reference gas space may also be caused by a distortion of the reference pump current due to leakage currents which may occur between the feeder line to the third electrode and feeder lines to a sensor heater, for example.

An object of the present invention is to provide a circuit configuration which permits reliable operation of a gas sensor having a reference gas space.

SUMMARY OF THE INVENTION

Accordingly, a diagnostic system containing a timer is provided. The diagnostic system delivers a current selection signal to a current source for setting the reference pump current in the diagnostic operation of the gas sensor and delivers a switching signal to the timer to start the timer. The diagnostic system evaluates a sensor signal of the gas sensor in the diagnostic operation based on time.

The circuit configuration according to the present invention increases the reliability of the sensor signal of the gas sensor. This eliminates unnecessary corrections and late corrections. In addition, any intervention measure that may be necessary, e.g., intervention into the setting of the reference pump current, may be limited to the required extent, so that overloading of the Nernst cell is prevented. Using the sensor signal permits a simple implementation of the circuit configuration according to the present invention.

Advantageous embodiments and refinements of the circuit configuration according to the present invention are derived from the dependent claims.

According to one embodiment, the diagnostic system evaluates the rate of change in the sensor signal. The time evaluation, in particular that of the rate of change, permits an evaluation of a poisoning rate or a leakage current.

According to one embodiment, the diagnostic system includes a comparator which compares the sensor signal with a threshold value and supplies a diagnostic signal as a function of the comparison result. The diagnostic signal may advantageously be used to stop the timer.

According to one refinement, an end signal that is supplied by the timer and reflects an elapsed period of time influences the reference pump current.

According to one embodiment, the time detectable by the timer is set at a maximum time. With this measure, it is possible to evaluate a low poisoning level or poisoning rate as well as low leakage currents at which the threshold would not be exceeded by the sensor signal within the maximum time. If the threshold is exceeded within the maximum time, a quantitative evaluation is possible.

A relevant diagnostic signal is obtained by operating the electrode of the reference gas space with a negative pump current. A negative pump current should mean that the reference gas is pumped out. With this measure it is possible to recognize even incipient poisoning or leakage currents. In particular, there is a great possibility of the threshold being exceeded within the maximum time, so that a quantitative evaluation of the poisoning, poisoning rate or leakage currents is possible.

A simple possibility of controlling the current source using the current selection signal is to provide a cutoff for the current source. A negative reference pump current is advantageously predefined, resulting in a targeted reduction in the concentration of the reference gas. Alternatively and/or additionally, the reference electrode may be switched to a predefined potential via a resistor. The potential is to be set in such a way that a discharge current flowing across the resistor constantly pumps the reference gas out to also reduce the concentration of the reference gas in a targeted manner.

The diagnostic result of the circuit configuration according to the present invention is expediently used to set the reference pump current outside of diagnostic operation, so as to counteract poisoning or compensate for a leakage current.

According to one embodiment, the gas sensor is a lambda sensor for determining an air/fuel ratio in combustion processes. The reference gas space then contains oxygen as the reference gas.

The lambda sensor is located in the exhaust gas system of an internal combustion engine or in a heating system, for example. According to one refinement based on the sensor being located in the exhaust gas system of an internal combustion engine, the diagnostic control system starts the diagnosis after a shutdown of the internal combustion engine.

DETAILED DESCRIPTION

Figure 1:
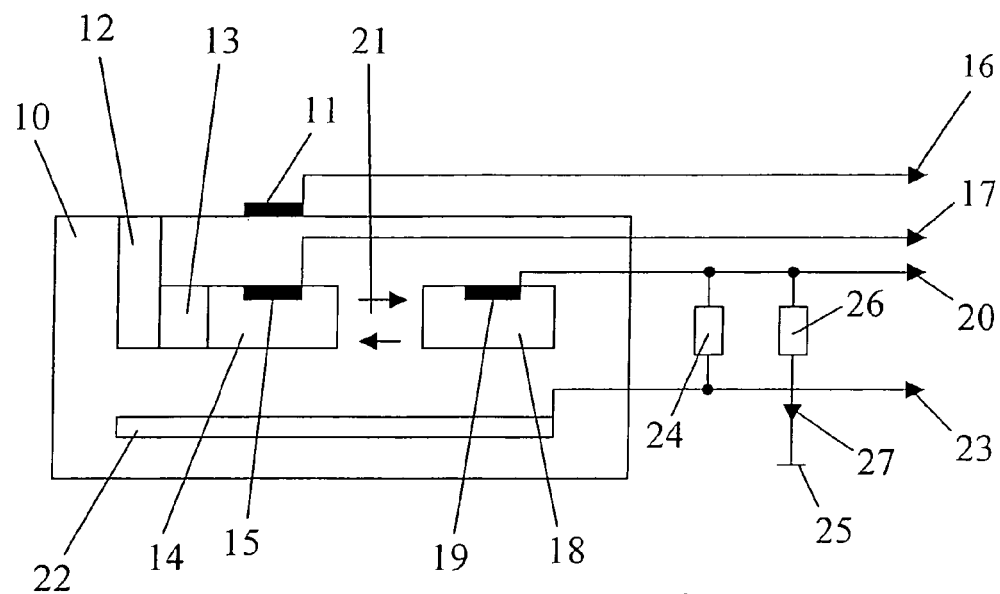
FIG. 1 shows a sectional view through a gas sensor.

Gas sensor 10 shown in FIG. 1 includes a first electrode 11 which is exposed to a gas to be analyzed. The gas to be analyzed passes through a gas channel 12 and a diffusion barrier 13 into a measuring gas space 14 in which a second electrode 15 is located. A pump cell is formed between first and second electrodes 11, 15. The first electrode is connected to a pump current line 16 and the second electrode is connected to a measuring line 17.

Gas sensor 10 includes a reference gas space 18 in which a third electrode 19 is located which is connected to a reference pump current line 20. A reference gas ion transport 21 may occur in a Nernst cell, which is formed between reference gas space 18 and measuring gas space 14.

Gas sensor 10 also includes a sensor heater 22 connected to a heater line 23. A parasitic resistor 24 is provided between heater line 23 and reference pump current line 20. A discharge current 27 flows across an ohmic resistor 26 connected between reference pump current line 20 and a potential 25.

Figure 2:
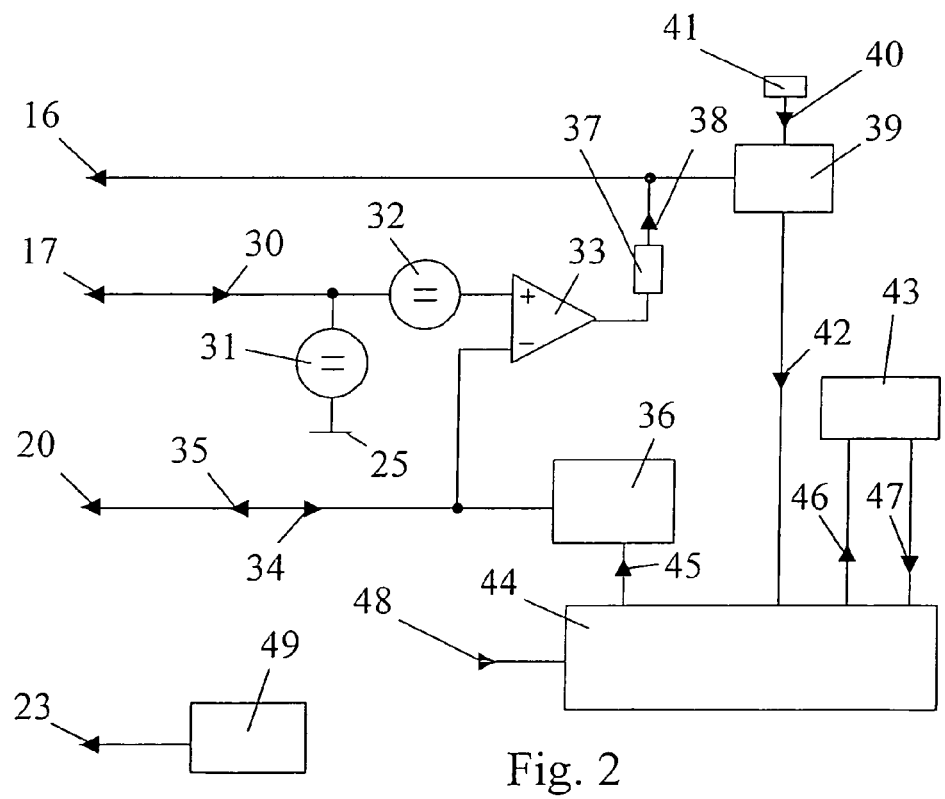
FIG. 2 shows a block diagram of a circuit configuration according to the present invention.

The block diagram of a circuit configuration according to the present invention shown in FIG. 2 illustrates pump current line 16, measuring line 17, reference pump current line 20 and heater line 23, which are identical to the lines labeled in the same way in FIG. 1.

Measuring line 17 carrying a first measuring signal 30 is connected to an offset voltage source 31 and to a reference voltage source 32. Reference voltage source 32 is connected to a non-inverting input of a difference amplifier 33.

Reference pump current line 20 carrying a second measuring signal 34 is at the same time conducting a reference pump current 35 provided by a current source 36. Reference pump current line 20 is connected to an inverting input of difference amplifier 33, whose output supplies a pump current via a working resistor 37. The pump current is identical to a sensor signal 38 sent to a comparator 39 which compares sensor signal 38 with a threshold value 40 provided by a threshold value generator 41.

Comparator 39 delivers a diagnostic signal 42 to current source 36 and to a diagnostic control system 44.

Diagnostic control system 44 delivers a first current selection signal 45 to current source 36 and a switching signal 46 to timer 43, which sends back an end signal 47 to diagnostic control system 44. Diagnostic control system 44 receives an enable signal 48.

Comparator 39, timer 43 and diagnostic control system 44 together form a diagnostic system. Heater line 23 is connected to a heater control unit 49.

Figure 3:
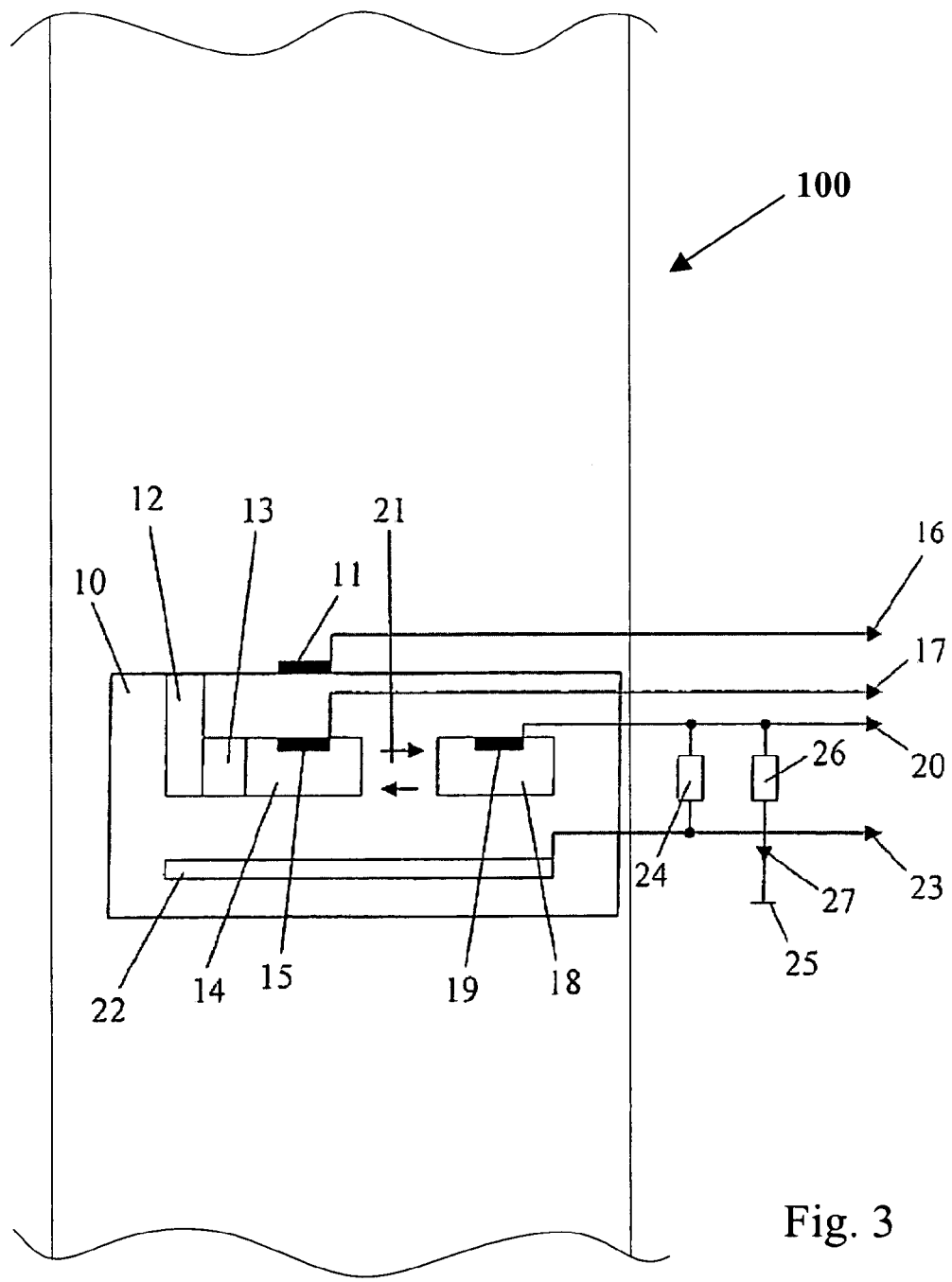
FIG. 3 shows a sectional view through the gas sensor located in the exhaust gas system of an internal combustion engine.

The circuit configuration according to the present invention functions as follows: First electrode 11 of gas sensor 10 is exposed to a gas to be analyzed. The gas may be an exhaust gas from a combustion process such as that occurring in a heating system operated with fossil fuels or in internal combustion engines, for example. In the following discussion, an exhaust gas from an internal combustion engine is assumed as an example, e.g., where the gas sensor 10 is located in an exhaust gas system 100 of the internal combustion engine as illustrated in FIG. 3. The exhaust gas passes through gas channel 12 and through diffusion barrier 13 into measuring space 14, which together with reference gas space 18 forms a Nernst cell which shows an abrupt voltage change in the area of combustion with a stoichiometric air/fuel ratio corresponding to a lambda factor of one. Reference gas space 18 must be filled with a reference gas, which is oxygen in the case of the exhaust gas of a combustion process.

The concentration of oxygen as the reference gas may be in a wide range in the case of the Nernst cell because the change in the residual oxygen content includes several decimal powers in passing through the area of stoichiometric combustion. Nevertheless, the goal is to at least approximately maintain a constant concentration of the reference gas to ensure a correct measurement result and therefore prevent a drop in the concentration.

A voltage occurring at the Nernst cell is sent to difference amplifier 33 via measuring line 17 and reference pump current line 20. First measuring signal 30 occurring on measuring line 17 is increased by reference voltage source 32 by an amount of approximately 450 mV. The choice of this amount achieves the result that difference amplifier 33 has a zero crossing plus a change of sign in passing through the voltage of the first measuring signal 30 in comparison with the voltage of second measuring signal 34 and this may be used to regulate the voltage at the Nernst cell to a value of approximately 450 mV, corresponding to a lambda value of approximately one.

The regulation is accomplished by influencing the oxygen concentration in measuring cell 14 via the pump cell formed between first and second electrodes 11, 15.

The output signal of difference amplifier 33 generates a pump current via working resistor 37, this current being sent to first electrode 11. A potential difference between first and second electrodes 11, 15 results in an oxygen ion current in the pump cell which is fixed with the pump current. With the help of diffusion barrier 13, an equilibrium may be established in measuring cell 14, so that the Nernst voltage between second electrode 15 of measuring gas space 14 and third electrode 19 of reference gas space 18 may be kept constant at the value of approximately 450 mV, for example, which is predefined by reference voltage source 32, presupposing the oxygen concentration in reference gas space 18 is kept at least approximately at a predefined value.

To do so, current source 36 is provided, supplying a reference pump current 35 to third electrode in reference gas space 18. Reference pump current 35 ensures that the oxygen concentration will be maintained by an oxygen ion transport 21 between measuring gas space 14 and reference gas space 18.

Diffusion processes may result in poisoning of reference gas space 18. Hydrocarbons diffused into reference gas space 18 bind oxygen through oxidation processes. Oxygen diffused out of reference gas space 18 lowers the oxygen concentration directly.

In addition, distortion of reference pump current 35 may occur due to leakage currents. Such leakage currents occur due to parasitic resistors 24, which are in effect between reference pump current line 20 and components having a lower potential than the potential on reference pump current line 20. As an example, FIG. 1 shows heater line 23 as a component having a lower potential so that parasitic resistor 24 is in effect here. The leakage currents depend on impurities in the materials used and in particular on the temperature, so that it is not readily possible to include them in determining the size of reference pump current 35. The unnoticed reduction in reference pump current 35 results in an unnoticed reduction in oxygen in reference gas space 18 due to pumping out the oxygen.

The occurrence of diffusion processes and leakage currents in particular is promoted by the fact that, due to offset voltage source 31 used here, the average potential on electrodes 11, 15, 18 is kept at a higher potential than would correspond to a ground potential. Offset voltage source 31 is set at half of the operating voltage of difference amplifier 33, for example. At an operating voltage of 5 V, the voltage of offset voltage source 31 is set at 2.5 V. With this measure, the potentials of first and second measuring signals 30, 34 are raised to levels that are easy to handle and differ at least significantly from a ground potential. Due to an increase in the voltage differences between the components, the voltage shift additionally increases any leakage currents that might be present to higher values.

A diagnosis of the concentration or the concentration change of the reference gas in reference gas space 18 or the leakage currents is made possible by the diagnostic system 39, 43, 44.

A diagnostic process takes place as follows:

When an enable signal 44 is received, diagnostic control system 44 starts the diagnosis by outputting current selection signal 45 to current source 36 and by outputting switching signal 46 to timer 43 to start the timing by timer 43.

Enable signal 48 may be triggered in the case of a gas sensor 10 situated in an exhaust gas system (not shown here) of an internal combustion engine (also not shown here), e.g., after shutdown of the engine. At this point in time, the probability is greatest that an elevated temperature will occur on gas sensor 10 and on lines 16, 17, 20, 23 resulting in increased diffusion processes and increased leakage currents. Enable signal 44 may also be triggered in other suitable operating states of the engine, such as idling.

Current selection signal 45 triggers current source 36 to change reference pump current 35, preferably to supply a lower reference pump current 34 than before the start of the diagnosis. A simple implementation is achieved when current source 36 is turned off, so that reference pump current 35 becomes zero. According to another possibility, the positive polarity of reference pump current 35 is reversed and a negative reference pump current 35 is set.

Reference pump current 35, which has been reduced or shut down entirely, may result in a decline in the concentration of the reference gas as a function of the conditions in reference gas space 18. In any case, negative reference pump current 35 results in a decline in the concentration of the reference gas.

Comparator 39 evaluates the pump current, which is sent to first electrode 11 and is a measure of sensor signal 38 of gas sensor 10. Instead of the current, the voltage drop at working resistor 37 may be used for analysis. The details are not important. It is essential that sensor signal 38 of gas sensor 10 is used for the diagnosis.

Comparator 39 compares sensor signal 38 with a threshold value 40 supplied by threshold value generator 41. The threshold value in the case of the exhaust gas of a combustion process, for example, may be set to a value which corresponds to an oxygen concentration in the exhaust gas to be analyzed of 21%, i.e., the maximum possible value. If sensor signal 38 exceeds this threshold, the oxygen concentration in reference gas space 18 is then definitely too low.

Timer 43 is preferably set for determining a maximum time. After the maximum time has elapsed, timer 43 delivers end signal 47 to diagnostic control system 44 in any case.

If the threshold has not been exceeded within the maximum time, diagnostic control system 44 may either leave current selection signal 45 unchanged on the basis of this diagnostic result or may alter it in such a way that current source 36 supplies a lower reference pump current 35.

If a threshold is exceeded within the maximum time, diagnostic signal 42 is triggered which may be used by diagnostic control system 44 to set current selection signal 45 which increases reference pump current 35 which is to be newly provided by current source 46 to counteract the poisoning or the elevated leakage current. The increase or decrease in pump current 35 to be implemented may be accomplished in steps between diagnostic procedures until reaching a predefined state in the reference gas space.

It is possible to ensure that sensor signal 38 will exceed the threshold within the maximum time by predefining a negative reference pump current 35 which results in a targeted decline in oxygen concentration in reference gas space 18. According to one refinement, negative reference pump current 35 may be adjusted independently from current source 36 by connecting reference pump current line 20 to a predefined potential 25 across ohmic resistor 26. Potential 25 is preferably the electric circuit ground, which, because of offset voltage source 31, is more negative than the potential prevailing on reference pump current line 20.

Diagnostic system 39, 43, 44 permits evaluation of the time change of sensor signal 38 during a diagnostic procedure. In particular the rate of change may be determined quantitatively via timer 43. The response of diagnostic signal 42 directly permits a new setting of reference pump current 35 to a value which ensures stable operation of gas sensor 10.

What is claimed is:

1. A circuit configuration for operating a gas sensor, comprising:
    a structure including a reference gas space;
    a reference electrode situated in the reference gas space;
    a current source for supplying a reference pump current to the reference electrode; and
    a diagnostic system including a timer, wherein the diagnostic system:
        delivers a current selection signal to the current source for setting the reference pump current during a diagnostic operation of the gas sensor;
        delivers a switch signal to the timer for starting the timer;
        evaluates a sensor signal of the gas sensor during diagnostic operation based on time; and
        evaluates a rate of change of the sensor signal.

2. The circuit configuration as recited in claim 1, wherein the diagnostic system includes a comparator that compares the sensor signal with a threshold value to produce a comparison result and supplies a diagnostic signal as a function of the comparison result.

3. The circuit configuration as recited in claim 2, wherein the diagnostic signal stops the timer.

4. The circuit configuration as recited in claim 1, further comprising:
    a resistor, wherein:
        the reference electrode is permanently connected to a predefined potential across the resistor, and
        a discharge current flowing across the resistor pumps out a reference gas.

5. The circuit configuration as recited in claim 1, wherein the gas sensor is a lambda sensor and the reference gas space contains oxygen as a reference gas.

6. The circuit configuration as recited in claim 5, wherein the lambda sensor is situated in an exhaust gas system of an internal combustion engine and an enable signal triggers the diagnosis after shutdown of the internal combustion engine.

7. A circuit configuration for operating a gas sensor, comprising:
- a structure including a reference gas space;
- a reference electrode situated in the reference gas space;
- a current source for supplying a reference pump current to the reference electrode; and
- a diagnostic system including a timer, wherein:
  - the diagnostic system delivers a current selection signal to the current source for setting the reference pump current during a diagnostic operation of the gas sensor;
  - the diagnostic system delivers a switch signal to the timer for starting the timer;
  - the diagnostic system evaluates a sensor signal of the gas sensor during diagnostic operation based on time;
  - the diagnostic system includes a comparator that compares the sensor signal with a threshold value to produce a comparison result and supplies a diagnostic signal as a function of the comparison result;
  - the diagnostic signal stops the timer;
  - the timer supplies an end signal that represents a time elapsed, and
  - the current selection signal is set as a function of the end signal for operating the gas sensor outside of the diagnostic operation.

8. The circuit configuration as recited in claim 7, wherein a time determinable by the timer is set at a maximum time.

9. The circuit configuration as recited in claim 7, wherein the current selection signal one of triggers the current source to supply a negative reference pump current and shuts down the current source.

10. The circuit configuration as recited in claim 7, further comprising:
- a resistor, wherein:
  - the reference electrode is permanently connected to a predefined potential across the resistor, and
  - a discharge current flowing across the resistor pumps out a reference gas.

11. The circuit configuration as recited in claim 7, wherein the gas sensor is a lambda sensor and the reference gas space contains oxygen as a reference gas.

12. The circuit configuration as recited in claim 11, wherein the lambda sensor is situated in an exhaust gas system of an internal combustion engine and an enable signal triggers the diagnosis after shutdown of the internal combustion engine.

* * * * *